United States Patent [19]

Makabe et al.

[11] Patent Number: 4,716,459
[45] Date of Patent: Dec. 29, 1987

[54] FATIGUE CRACK POSITION DETECTION APPARATUS

[75] Inventors: Eiichi Makabe; Mitsuaki Uesugi; Masaichi Inomata; Kyusuke Maruyama; Kenji Iwai, all of Yokohama; Kazuo Sano, Tokyo, all of Japan

[73] Assignee: Nippon Kokan Kabushiki Kaisha, Tokyo, Japan

[21] Appl. No.: 912,582

[22] PCT Filed: Jan. 24, 1986

[86] PCT No.: PCT/JP86/00028
§ 371 Date: Sep. 16, 1986
§ 102(e) Date: Sep. 16, 1986

[87] PCT Pub. No.: WO86/04410
PCT Pub. Date: Jul. 31, 1986

[30] Foreign Application Priority Data

Jan. 25, 1985 [JP] Japan ................... 60-12098
Oct. 25, 1985 [JP] Japan ................. 60-239025
Oct. 25, 1985 [JP] Japan ................. 60-239026

[51] Int. Cl.$^4$ ................... H04N 7/18; G01N 19/08
[52] U.S. Cl. ................... 358/106; 73/799
[58] Field of Search ................... 73/799, 800; 358/106, 358/107, 93; 358/93

[56] References Cited

U.S. PATENT DOCUMENTS

| 4,003,246 | 1/1977 | Cain | 73/799 |
| 4,149,406 | 4/1979 | Russenberger | 73/775 |
| 4,305,096 | 12/1981 | Yokoshima et al. | 358/106 |
| 4,364,113 | 12/1982 | Sengebusch et al. | 358/106 |
| 4,446,481 | 5/1984 | Edamatsu et al. | 358/106 |
| 4,574,642 | 3/1986 | Fleischman | 73/799 |
| 4,613,234 | 9/1986 | Cruickshank | 358/106 |

FOREIGN PATENT DOCUMENTS

| 57-15286 | 1/1982 | Japan . |
| 57-92840 | 11/1982 | Japan . |
| 58-23991 | 5/1983 | Japan . |
| 2057124 | 3/1981 | United Kingdom | 73/799 |
| 2108684 | 5/1983 | United Kingdom | 73/799 |

Primary Examiner—Michael J. Tokar
Assistant Examiner—Robert R. Raevis
Attorney, Agent, or Firm—Frishauf, Holtz, Goodman & Woodward

[57] ABSTRACT

A distance between a distal end of a crack formed in a fatigue test piece on which a reference line is scribed, and the reference line, is monitored. The reference line and the crack are scanned with an ITV camera to prepare the fatigue test piece having the crack of a predetermined length. Luminance levels are integrated from a video signal obtained by scanning each raster in the same direction as that of the reference line to obtain a maximum luminance level, and the reference line position is detected from the maximum luminance level. At the same time, continuity of a high-level value is discriminated from the video signal, and a crack distal end position is detected from the discrimination result. A difference between both the detected positions is calculated, and the test piece is machined so that the difference corresponds to the predetermined length.

6 Claims, 10 Drawing Figures

FATIGUE CRACK POSITION DETECTION APPARATUS

TECHNICAL FIELD

The present invention relates to a fatigue crack position detection apparatus for detecting a distal end position of a crack in a test piece used in a fatigue test for metal material.

BACKGROUND ART

Figure 2:
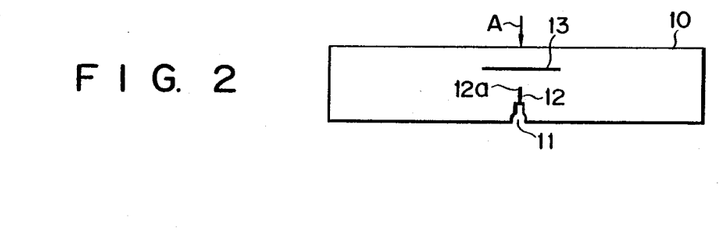
FIG. 2 is a side view of a fatigue test piece.

Measurement of fatigue of a metal material uses fatigue test piece 10 in which fatigue crack 12 is formed, as shown in FIG. 2. The shape and size of piece 10 are defined in, e.g., B. S. 5762-1979 (Methods for crack opening displacement testing). Test piece 10 is defined such that crack 12 having a predetermined length is formed from the bottom portion of notch 11 formed in the central portion of piece 10. During formation of crack 12, a load must be applied on test piece 10 while observing the length, i.e., the distal end position of crack 12.

Various conventional methods for detecting the distal end position of crack 12 have been used. Among these methods, noncontact detection methods are preferable. The noncontact detection methods include a method for optically monitoring crack 12 and a method for detecting a magnetic change caused by crack 12 as a change in eddy current, if piece 10 is a magnetic substance. However, in the method using the eddy current, the detection result varies in accordance with the magnetic characteristics of the piece, and a crack position cannot be precisely detected. Therefore, demand has arisen for an apparatus which can precisely and easily detect a crack position by an optical method.

DISCLOSURE OF INVENTION

It is an object of the present invention to provide a fatigue crack position detection apparatus which can detect a distal end position of a crack formed in a fatigue test piece in a noncontact manner.

According to the present invention, there is provided a method for automatically measuring a crack distal end position in a fatigue test piece, characterized in that luminance levels are integrated from an image signal obtained by scanning a reference line and a crack formed in a fatigue test piece in the same direction as that of the reference line so as to obtain a reference line position from a maximum luminance level. The image signal is converted into a binary signal to detect a crack distal end position by discriminating continuity of a high-level value, and a distance between the reference line position and the crack distal end position is then calculated.

According to the present invention, there is provided an apparatus for automatically measuring a crack distal end position of a fatigue test piece, characterized by comprising: scanning means for scanning a reference line and a crack in a fatigue test piece with the reference line, for obtaining a crack distal end position within an identical field of view; reference line detection means for integrating luminance levels from a video signal obtained by a scanning operation of the scanning means in the same direction as that of the reference line to obtain a maximum level to detect a reference line position; crack distal end position detection means for binary-coding the luminance levels of the video signal output from the scanning means in a direction perpendicular to a direction of the crack and thereafter discriminating continuity of a high-level value to detect a crack distal end position; and crack distal end position calculating means for calculating a distance between the reference line position obtained by the reference line detection means and the crack distal end position obtained by the crack distal end position detection means.

BRIEF DESCRIPTION OF THE DRAWINGS

FIG. 4($a$) is a view of an image of a test piece;

FIG. 4($b$) is a graph showing luminance distribution along the vertical direction of a test piece image;

FIGS. 5($a$) to 5($d$) are views showing a crack detecting operation;

FIGS. 6($a$) to 6($c$) are views showing a noise removing operation during crack detection;

FIGS. 9($a$) to 9($d$) are timing charts for explaining the operation of the apparatus shown in FIG. 8.

BEST MODE FOR CARRYING OUT THE INVENTION

An embodiment of the present invention will be described hereinafter with reference to the accompanying drawings.

Figure 1:
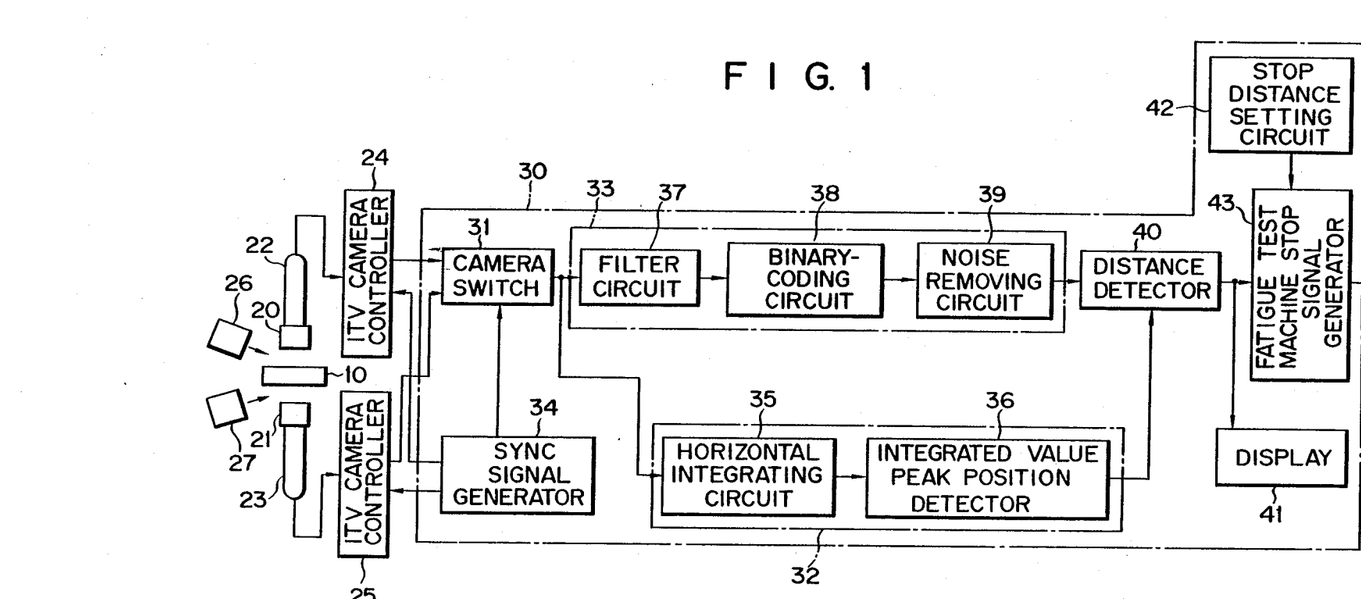
FIG. 1 is a block diagram of a fatigue crack position detection apparatus according to an embodiment of the present invention.

Referring to FIG. 1, microscopes 20 and 21 are arranged to set both the surfaces of fatigue test piece 10 within their fields of view. Optical images obtained by microscopes 20 and 21 are scanned by industrial TV camera (ITV) heads 22 and 23. The operations of ITV camera heads 22 and 23 are respectively controlled by ITV camera controllers 24 and 25. Both surfaces of test piece 10 are obliquely irradiated with light from light sources 26 and 27, respectively.

In test piece 10, as shown in FIG. 2, notch 11 is formed in the central portion of its lower side, and crack 12 having a predetermined length is formed from the bottom portion of notch 11. Crack 12 is formed by, e.g., applying a load on the surface directly opposite the surface in which notch 11 is formed in the direction indicated by arrow A, while holding the two ends of piece 10. The length, i.e., the distal end, of crack 12 is detected by a distance between line 13 scribed with a diamond scriber and itself. It is preferable that the surface on which line 13 is scribed is sufficiently polished to obtain a mirror surface.

Figure 3:
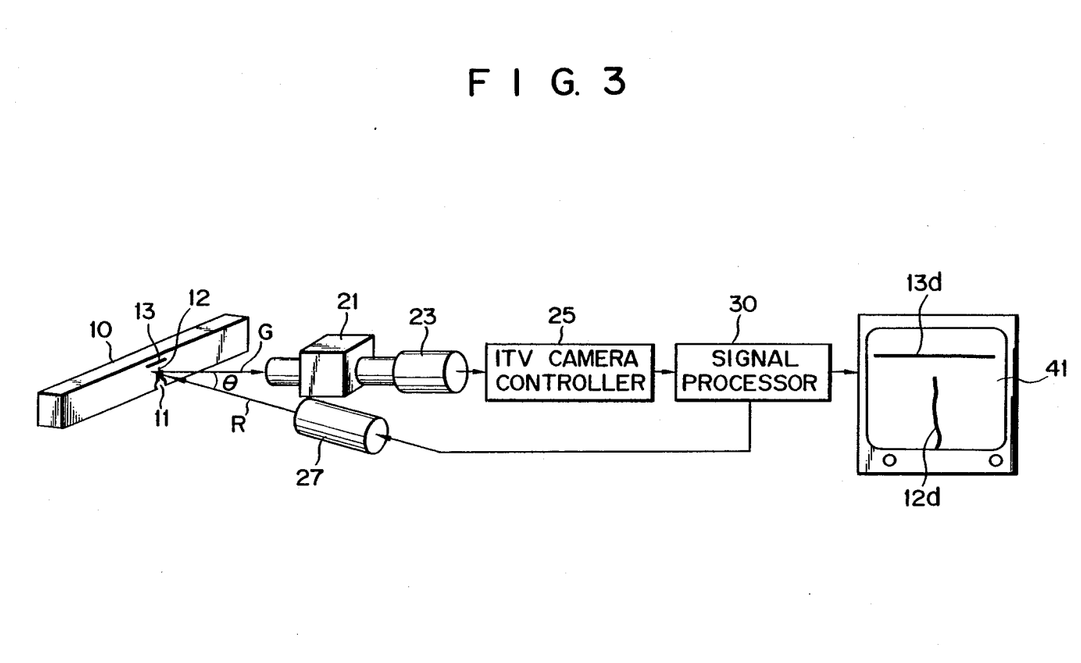
FIG. 3 is a perspective view partially showing the apparatus shown in FIG. 1.

FIG. 3 illustrates this portion in detail. Optical axis G of microscope 21 is substantially perpendicular to the surface of test piece 10, and light R from light source 27 is incident on the surface of test piece 10 at predetermined angle $\theta$ with respect to optical axis G. Therefore, microscope 21 receives only light reflected by portions, e.g., line 13, scratches, and the like, which irregularly reflect incident light R. Note that the direction of line 13 preferably coincides with the horizontal scanning directions of ITV camera heads 22 and 23. ITV camera heads 22 and 23 scan images of test piece 10 which are enlarged through microscopes 20 and 21 under the control of ITV camera controllers 24 and 25, respectively. Video signals from heads 22 and 23 are supplied to signal processor 30 respectively through controllers 24 and 25, and are then supplied to line detection means 32 and crack distal end position detection means 33 through camera switch 31. Note that reference numeral 34 denotes a sync signal generator for supplying a sync signal to controllers 24 and 25 and switch 31.

Line detection means 32 integrates the luminance level of the video signal in the same direction as that of line 13 for each raster to obtain a maximum luminance level for one frame, thereby detecting a line position from a raster position at which the maximum luminance level is obtained. Line detection means 32 comprises horizontal integrating circuit 35 and integrated value peak position detector 36.

Crack distal end position detection means 33 converts the video signal into a binary signal and, thereafter, checks if a high level value is continuously generated from image data obtained from the binary signal and satisfies a given continuity condition, thereby detecting crack 12. Crack distal end position detection means 33 comprises filter circuit 37, binary-coding circuit 38 and noise removing circuit 39.

Reference numeral 40 denotes a distance detector. Distance detector 40 obtains a distance between the line position and the crack distal end position obtained by means 32 and 33. Crack image 12d, line image 13d, and the distance therebetween are displayed on display 41, as shown in FIG. 3.

In addition, the apparatus of the present invention comprises stop distance setting circuit 42 prestoring a set value of a distance between line 13 and the crack distal end position for stopping a fatigue test machine (not shown), and fatigue test machine stop signal generator 43 for supplying a stop signal to the fatigue test machine.

Figure 4:
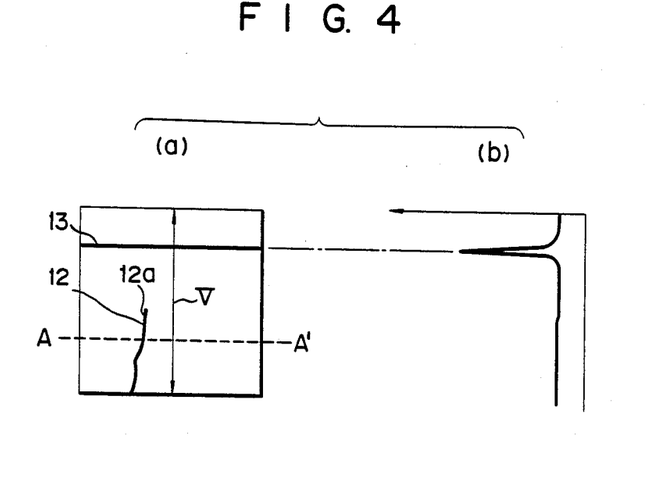

The operation of the apparatus with the above arrangement will now be described. ITV camera heads 22 and 23 set images of line 13 and crack 12 on the surfaces of test piece 10 enlarged by microscopes 20 and 21 within their fields of view. Image positions and the like are adjusted to obtain an image shown in FIG. 4(a). Illuminances of light sources 26 and 27 are varied to uniformly scan line 13 and crack 12 in white light. Note that the black and white portions of the image in FIG. 4(a) are reversed for the sake of simplicity.

The video signals of the images are supplied to line detection means 32 and crack distal end position detection means 33 through ITV camera controllers 24 and 25 and camera switch 31.

Line detection means 32 obtains an integrated value of luminance level of the video signal for each horizontal scanning period, i.e., for each raster. More specifically, the integrated value of the luminance level is obtained in the same direction as that of line 13 in the image shown in FIG. 4(a). Luminance distribution in vertical direction V shown in FIG. 4(b) is then obtained. Integrated value peak position detector 36 detects the maximum luminance level from the luminance distribution to obtain the position of line 13. Since crack 12 is also scanned in white light, it has a high luminance level. However, the luminance level by crack 12 is negligible since integration is performed in the direction of line 13.

For example, vertical size V of each field of view of ITV camera heads 22 and 23 is 5 mm, and the number of scanning lines of heads 22 and 23 is 480. Since an interlaced scanning system is adopted, one frame consists of 240 rasters. Therefore, the width of a raster is about 20 $\mu$m. In contrast to this, since the width of line 13 is about 100 $\mu$m, an image signal of line 13 can be obtained within four to five rasters.

For example, a video signal obtained from ITV camera head 22 is selected by camera switch 31, and is then supplied to horizontal integrating circuit 35 and filter circuit 37. Horizontal integrating circuit 35 integrates the luminance level of each of 240 rasters, and sequentially stores the integrated value in a memory having 240 address positions corresponding to the number of rasters. The luminance level integrated values for the respective rasters stored in the memory are sequentially supplied to integrated value peak position detector 36 for every address of the memory, and the peak value is detected. Assume that peak values are obtained between the 96th raster to 100th raster of the 240 rasters (counted from the upper raster). Detector 36 can hold addresses in this internal, i.e., the 96th to 100th memory addresses. The above operation can be easily realized by constituting line detection means 32 by a microcomputer.

Figure 5:
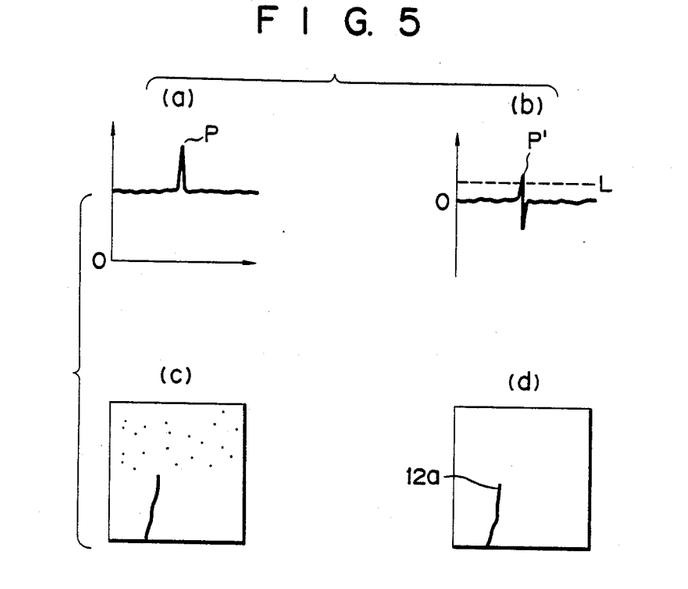

Crack distal end position detection means 33 performs the following operation. The video signal on line A—A' shown in FIG. 4(a) has a high level corresponding to crack portion P, as shown in FIG. 5(a). The video signal is passed through high-pass filter circuit 37 to remove a DC component therefrom so as to emphasize crack portion P and not to be influenced by a change in the entire luminance level (e.g., caused by changing an object to be measured). The video signal passed through high-pass filter circuit 37 has a waveform, e.g., as shown in FIG. 5(b), and is supplied to binary-coding circuit 38 to be binary-coded, thereby detecting pulse signal P' corresponding to crack 12. More specifically, binary-coding circuit 38 detects the maximum value of the video signal for each raster and, therefore, determines that crack 12 is present at a position on the raster at which the maximum value is detected. However, it is nonsense to detect the maximum level on a scanning line on which no crack 12 is present. Thus, threshold level L is set and maximum value detection is performed with respect to signals exceeding threshold level L. FIG. 5(c) shows an image obtained from the binary signal. However, threshold level L does not satisfactorily extract only crack 12, and the resultant image data includes a noise component. The noise component includes scratches formed when piece 10 is polished. In addition, in the line 13 portion, the same waveform as that of the crack portion is formed and is erroneously detected as noise.

The noise component is removed by noise removing circuit 39. More specifically, noise removing circuit 39 uses window W shown in FIG. 6(a). Window W extends vertically and horizontally in given lengths from given point B. If the number of high levels (maximum values) within window W, i.e., the density of a point within window W exceeds a certain value, the point is determined as a part of crack 12; otherwise, it is determined as a noise component and erased.

Figure 6:
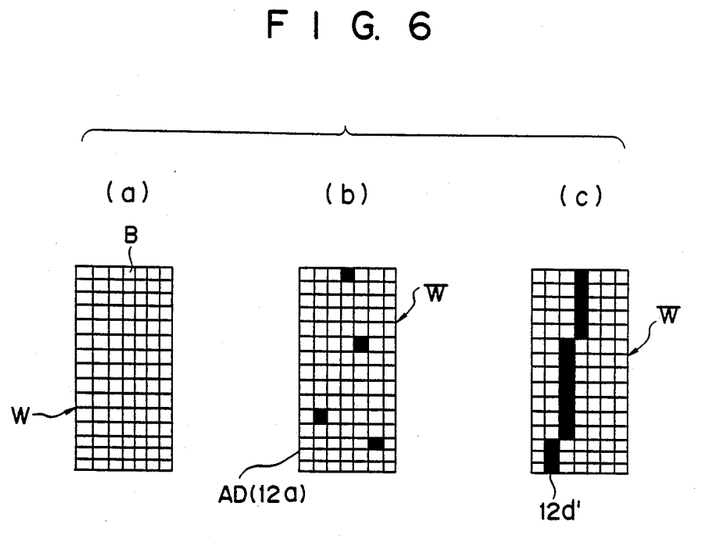

More specifically, it is checked if a high-level portion is continuously generated. FIG. 6(b) shows binary signal levels in noise component portion Q1 shown in FIG. 7, and reveals that high-level portions (indicated by black dots in FIG. 6(b)) are discontinuous. FIG. 6(c) shows portion Q2 of crack 12, and reveals that the high-level portions are continuously generated. When the noise component is removed as described above, the resultant image is shown in FIG. 5(c). Then, distal end position 12a of crack 12 is detected. During detection, the threshold value of the window density is decreased to reduce a possibility for detecting crack 12 as a noise component.

Figure 7:
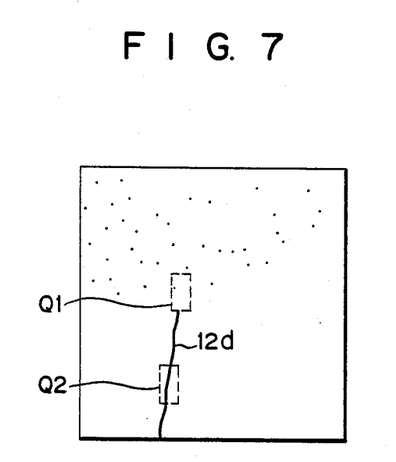
FIG. 7 is a view showing the relationship between a window shown in FIG. 6 and a test piece image.

The video signal obtained from binary circuit 38 for each raster as shown in FIG. 5(b) is supplied to noise removing circuit 39. In circuit 39, the input video signal is sampled using sampling pulses having a pulse rate which divides one horizontal scanning period (1H) into 256 subperiods, and the sampling outputs are stored in a dot memory having 256 horizontal address positions and 240 vertical address positions. The video signal for one frame stored in the dot memory is subjected to noise removal using a 7 (row dots)×15 (column dots) partial memory as window W. More specifically, if the number of black dots within window W is below a predetermined value, as shown in FIG. 6(b), the black dots within window W are determined as noise components and are erased. If the number of black dots exceeds the predetermined number, as shown in FIG. 6(c), they are determined as the image of crack 12 and are left unchanged. For example, crack portion Q2 in FIG. 7 is extracted within window W as shown in FIG. 6(c). When window W is moved along crack image 12d from the position shown in FIG. 6(c) crack image 12d is extinguished and noise portion Q1 appears. Therefore, as shown in FIG. 6(b), lower end address AD(12a) in the vertical direction of window W when noise portion Q1 is detected is stored as data representing the vertical position of distal end 12a of crack 12. Noise removing circuit 39 can also be constituted by a microcomputer, as in the case of line detection means 32. More specifically, the video signal output from binary circuit 38, i.e., obtained from the state shown in FIG. 5(b), is sampled as 256 digital data, and then input to circuit 39. In noise removing circuit 39, 256 stages of first and second registers are horizontally arranged, and data for 240 vertical rasters are sequentially input to the first and second registers. The contents of the first and second registers are compared at every stage. If there are data corresponding to a crack in the vertical direction, the contents of the first and second registers coincide with each other, and are held as crack data. The above operation is sequentially performed downward with respect to data for 240 rasters, and a vertical memory address corresponding to a raster from which a coincidence is first found is used as position data of distal end 12a of the crack.

The line position and crack distal end position obtained by means 32 and 33 are supplied to distance detector 40. A distance between line 13 and crack distal end position 12a is calculated by distance detector 40 as a difference between their addresses, and is displayed on display 41. The distance is compared with a distance set in stop distance setting circuit 42. When the calculated distance is smaller than the set distance, stop signal generator 43 sends fatigue test stop signal K to the fatigue test machine, thereby releasing a load applied on test piece 10.

In this embodiment, the maximum luminance level is obtained by line detection means 32 from the video signals of test piece 10 scanned through microscopes 20 and 21 to detect the position of line 13. Meanwhile, crack distal end position detection means 33 converts the video signal into a binary signal, and then checks continuity of a high level to extract the image of crack 12, thereby detecting the position of crack distal end 12a. Distance detector 40 then calculates the distance between line 13 and crack distal end position 12a with reference to the position of line 13 and the crack distal end position. Therefore, the following effects can be provided.

(1) When the position of line 13 on test piece 10 is preset, the position of crack distal end 12a on piece 10 can be automatically measured.

(2) The position of crack distal end 12a can be measured in a noncontact manner.

(3) If ITV camera heads 20 and 21 have the fields of view of a uniform size, since the crack distal end position can be measured without being influenced by a difference in shape or type of metals of test piece 10, no calibration is needed even if test piece 10 is changed.

(4) Upon switching of camera switch 31, cracks in both the surfaces of test piece 10 can be detected. Although not shown, if an averaging circuit is arranged at the output side of distance detector 40, the average value of the crack distal end positions on both the surfaces can be measured as the crack distal end position of the corresponding test piece.

In this embodiment, the above operation can be individually performed for the two ITV cameras. When cracks 12 in both the surfaces of single test piece 10 are to be detected, distances of two cracks and lines are calculated from images obtained by the two ITV cameras and their averaged value is detected to obtain the distance.

According to the present invention as described above, an automatic measuring apparatus which can automatically measure a crack distal end position of a fatigue test piece with high precision can be provided.

Figure 8:
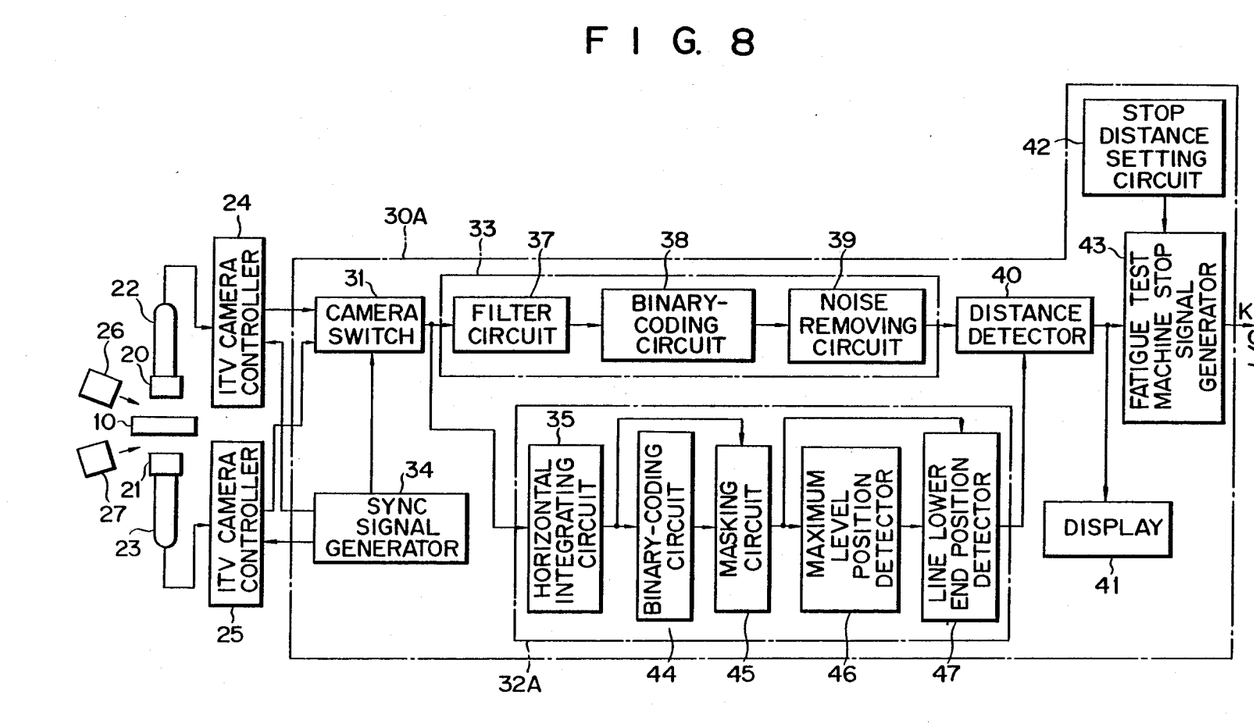
FIG. 8 is a block diagram of a fatigue crack position detection apparatus according to another embodiment of the present invention.

In the above embodiment, the width of line 13 is about 100 μm, and the width of a raster is 20 μm, and a video signal corresponding to line 13 is obtained from four to five rasters. Therefore, the most proper distance between line 13 and crack distal end 12a is one between the raster closest to crack distal end 12a among four to five rasters including the video signal of line 13, i.e., the lower end of line 13 and crack distal end 12a. FIG. 8 shows an embodiment capable of detecting the distance between the lower end of line 13 and crack distal end 12a. The same reference numerals in FIG. 8 denote the same parts as in FIG. 1, and a detailed description thereof will be omitted.

Figure 9:
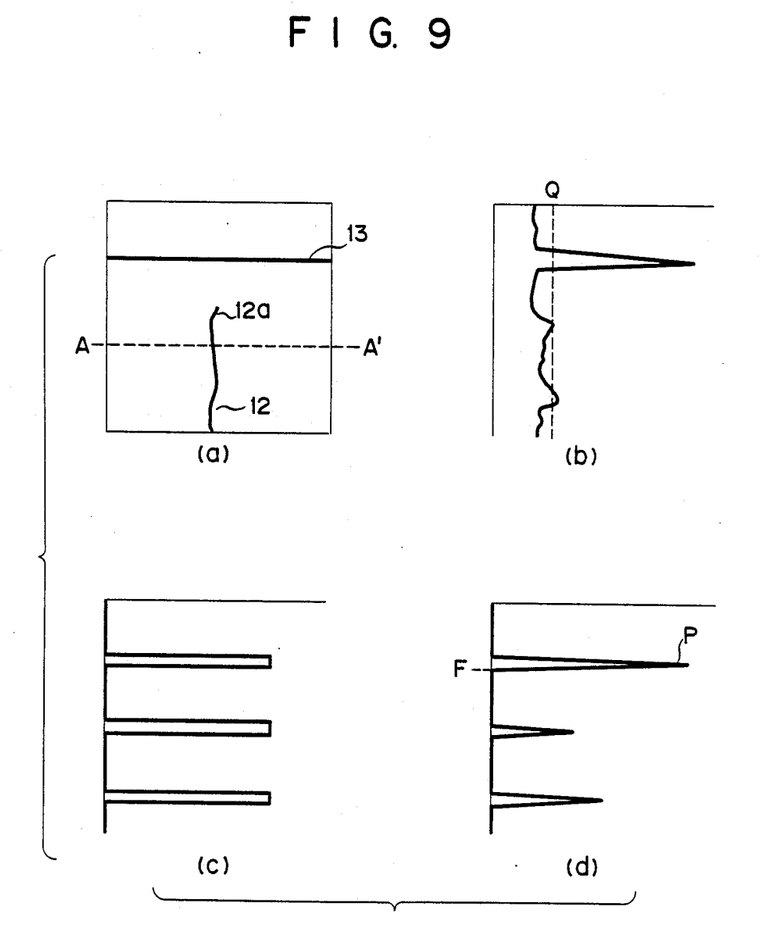

Referring to FIG. 8, line detection means 32A adopts the method of the above embodiment, and obtains average luminance levels in the same direction as that of line 13 from the video signals for the respective rasters obtained by scanning test piece 10 during the fatigue test. The average luminance levels are binarized using an optimal position for the fatigue test in the widthwise direction of the line (in this case, threshold level Q corresponding to the lower end position of line 13, as shown in FIG. 9(b)). The average luminance levels are then masked by the binary data to detect an optimal position for the fatigue test. More specifically, means 32A comprises horizontal integrating circuit 35 for obtaining the average luminance levels for the respective rasters in the same direction as that of line 13 from the video signals from ITV camera heads 22 and 23, binary circuit 44 for binary-coding the average luminance levels obtained from circuit 35 with reference to threshold level Q corresponding to the lower end position of the line most suitable for the fatigue test, masking circuit 45 for masking the average luminance levels using the binary data obtained by circuit 44, maximum level position detection circuit 36 for detecting a maximum level position from the masked data, and line lower end position detection circuit 47 for detecting a line lower end position from the maximum level position detected by circuit 36 and the masked data.

Line detection means 32A detects the line lower end position as follows. First, horizontal integrating circuit 35 calculates an integrated value of a luminance level of the video signal from each raster. More specifically, in an image shown in FIG. 9(a), integrated values of the luminance levels in the same direction as that of line 13 are calculated and their averaged values are then calculated. In this way, a vertical distribution of the luminance levels shown in FIG. 9(b) can be obtained. The averaged luminance levels are supplied to binary circuit 44, and are coded into binary data using threshold value Q corresponding to the line lower end position. Thus, the binary data shown in FIG. 9(c) is obtained. In masking circuit 45, the averaged luminance levels are masked by the binary data, thereby obtaining data shown in FIG. 9(d). The resultant data is supplied to maximum level position detection circuit 46, and the maximum level in the data, i.e., high-level position P corresponding to line 13, is detected. Data corresponding to the remaining high-level portions are not determined as line 13, and are canceled. High-level portion P corresponding to line 13 can thus be detected from the binary data. Line lower end position detection circuit 47 receives the masked data shown in FIG. 9(d) and the data of maximum high-level position P to detect line lower end position F as a memory address corresponding thereto.

In this embodiment, an averaged luminance level for each raster in the same direction is obtained from the video signal obtained by scanning test piece 10 with line 13 during the fatigue test. The averaged luminance levels are binary-coded using threshold level Q corresponding to a position most suitable for the fatigue test in the widthwise direction of the line 13. The averaged luminance levels are masked by the binary data. Therefore, the lower end position of line 13 most suitable for the fatigue test can be reliably detected. The most suitable position of the fatigue test, i.e., the position of line 13 may be determined between the tip of notch 11 and a position of the side surface of test piece 10 at which a load is applied in the direction of arrow A as shown in FIG. 2 so that crack 12 may be extended from the tip of notch 11 to line 13, when the load is applied to test piece 10. The position of line 13 can be detected not as the lower end but as an upper end position of the line width in accordance with fatigue test conditions. In addition, if threshold level Q is decreased not to pick up a noise component of the video signal, the lower and upper end positions of the line can be more precisely detected.

With this embodiment, the timing when crack distal end 12a reaches the lower end position of line 13 can be reliably detected, and the fatigue test machine can be stopped at this timing. The fatigue test machine can be stopped under the same conditions, thus improving precision of the fatigue test and reliability.

Test piece 10 with line 13 as a reference line shown in FIG. 2 is placed on the fatigue test machine and a load is repetitively applied thereto to form crack 12. Note that this load has a magnitude sufficient to vibrate piece 10, with an amplitude of several hundreds of microns and a frequency of about 30 Hz. When such a load is applied, the surfaces of test piece 10 are illuminated and are scanned by ITV cameras 22 and 23 through microscopes.

However, in the apparatus of this embodiment, since test piece 10 is illuminated with continuous light, the resultant image of test piece 10 is blurred. As described above, the load has a magnitude sufficient to vibrate piece 10, with an amplitude of several hundreds of microns and a frequency of about 30 Hz. In contrast to this, the fields of view of ITV camera heads 22 and 23 must be several millimeters, taking a resolution into consideration. Therefore, if the test piece 10 is scanned using continuous illumination, the resultant image is blurred due to vibration of piece 10, and the position of crack distal end 12a cannot be precisely detected.

The width of crack 12 formed in test piece 10 varies from several microns to several tens of microns in accordance with internal and surface conditions of piece 10. A portion of crack 12 having a small width must be illuminated at an appropriate illuminance, and if not, it cannot be scanned or detected.

Figure 10:
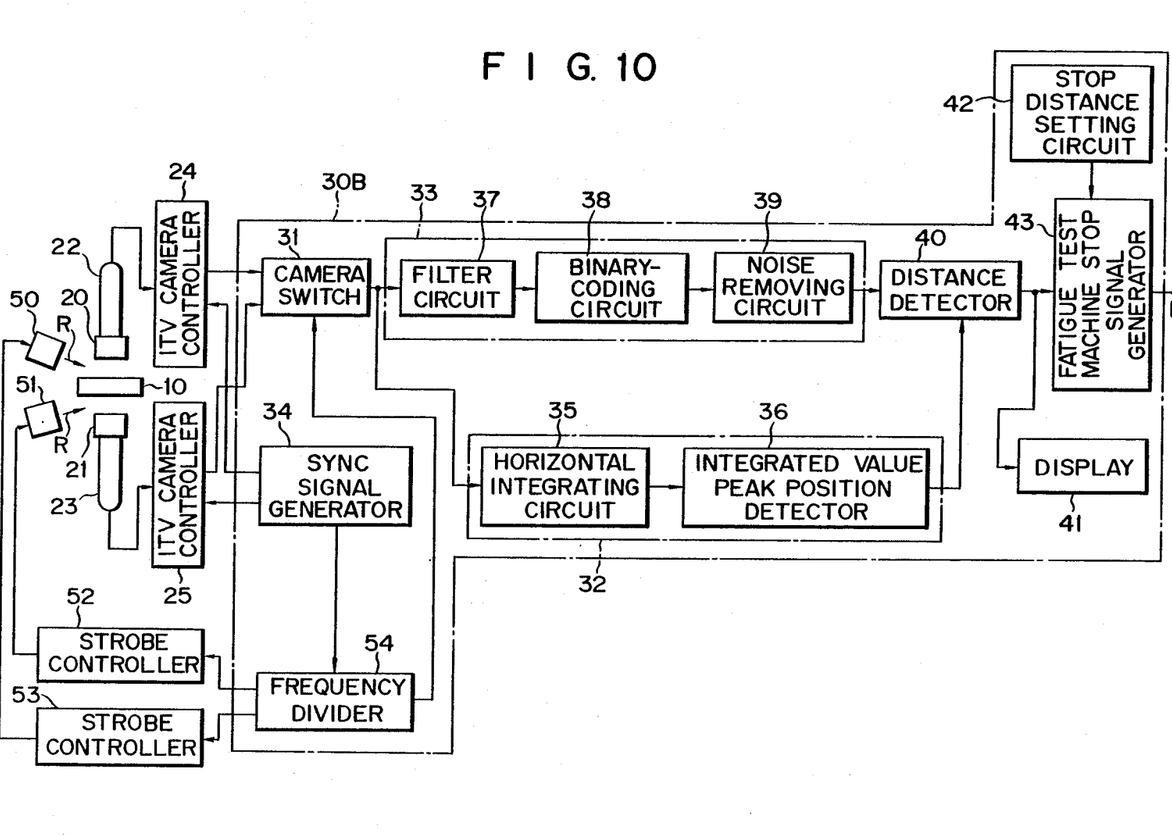
FIG. 10 is a block diagram of a fatigue crack position detection apparatus according to still another embodiment of the present invention.

In an embodiment shown in FIG. 10, a fatigue crack position detection apparatus which can be free from image blurring and can accurately detect a crack distal end position without being blurred if a vibrating test piece is scanned, can be provided.

With this embodiment, there is provided a fatigue crack position detection apparatus characterized by comprising: scanning means for scanning a reference line and a crack in a fatigue test piece with the reference line for obtaining a crack distal end position within an identical field of view; a strobe illumination device for irradiating the fatigue test piece with illumination light; illumination control means for controlling an emission timing of the strobe illumination device to a predetermined timing; reference line detection means for integrating luminance levels from a video signal obtained by a scanning operation of the scanning means in the same direction as that of the reference line to obtain a maximum level to detect a reference line position; crack distal end position detection means for binary-coding the luminance levels of the video signal output from the scanning means in a direction perpendicular to a direction of the crack and thereafter discriminating continuity of a high-level value to detect a crack distal end position; and crack distal end position calculating means for calculating a distance between the reference line position obtained by the reference line detection means and the crack distal end position obtained by the crack distal end position detection means.

Since the apparatus of this embodiment comprises the above-mentioned means, when a fatigue test piece is illuminated with light from the strobe illumination device, the fatigue test piece is scanned, and the reference line and the crack distal end position are detected from the resultant video signal to calculate the distance between the reference line and the crack distal end position.

Referring to FIG. 10, reference numerals 50 and 51 denote strobe illumination devices, which illuminate the surfaces of test piece 10 from positions inclined with respect to optical axes G of microscopes 20 and 21 at a predetermined angle $\theta$, e.g., 30°. Strobe illumination devices 50 and 51 emit light at time intervals sufficient to attenuate after-images in ITV camera heads 22 and 23. More specifically, an illumination control means comprises frequency divider 54 for dividing the sync signal from sync signal generator 34 for supplying the sync signal at a predetermined frequency division ratio, and strobe controllers 52 and 53 for causing strobe illumination devices 50 and 51 to emit light in response to the frequency-divided output from frequency divider 54. Note that camera switch 31 alternately passes the video signals from ITV camera heads 22 and 23 in synchronism with the emission operations of strobe illumination devices 50 and 51 in response to the frequency-divided output from frequency divider 54.

Referring to FIG. 10, when the sync signal is supplied from sync signal generator 34, ITV camera heads 22 and 23 start a scanning operation under the control of ITV camera controllers 24 and 25, respectively, and generate video signals.

At the same time, the sync signal is frequency-divided by frequency divider 54, and is output as a frequency-divided signal having a cycle twice an after-image time of ITV camera heads 22 and 23. Therefore, when the frequency-divided signal is alternately supplied to strobe controllers 52 and 53, strobe illumination devices 50 and 51 alternately emit light in synchronism with the frequency-divided signal. Strobe illumination devices 50 and 51 emit light at time intervals longer than the after-image time of ITV camera heads 22 and 23. Upon emission of strobe illumination device 50 or 51, the video signal is supplied to line detection means 32 and crack distal end detection means 33 through camera switch 31.

Note that an image is intermittently displayed on display 41 since it is obtained when strobe illumination devices 50 and 51 emit light. Therefore, if an image memory is added to store image data for one frame, a surface image of test piece 10 can be displayed as a still image, and an operator can be free from inconvenience during monitoring.

In this embodiment, when fatigue test piece 10 is illuminated with strobe illumination light from strobe illumination devices 50 and 51, it is scanned by ITV camera heads 22 and 23. Line 13 and crack distal end position 12a are detected from the resultant video signals to calculate the distance therebetween. Therefore, crack distal end position 12a can be accurately measured without blurring the scanned image of fatigue test piece 10. Since test piece 10 is scanned at an instant when illumination devices 26 and 27 emit light, an image can be obtained without being blurred even if test piece 10 vibrates. In addition, since emission timings of strobe illumination devices 50 and 51 are set to be longer than the after-image time of ITV camera heads 22 and 23, measurement can be free from an influence of an after-image.

We claim:

1. A method of detecting a fatigue crack position on a fatigue test piece on which a reference line is scribed, which comprises:
   integrating luminance levels in the same direction as that of the reference line from an image signal,
   obtaining the image signal by scanning said reference line and a crack formed in the fatigue test piece,
   obtaining a reference line position from a maximum luminance level in the image signal.
   converting the image signal into a binary signal,
   detecting a crack distal end position by discriminating a state in which a high-level value of the binary signal is continuously detected, and
   calculating a distance between the reference line position and the crack distal end position.

2. A fatigue crack position detection apparatus, which comprises:
   scanning means for scanning a reference line and a crack in a fatigue test piece, and for obtaining a crack distal end position within a field of view of the scanning means;
   reference line detection means for integrating luminance levels from a video signal output obtained by a scanning operation of said scanning means in the same direction as that of the reference line to obtain a maximum level in the luminance levels, and to detect a reference line position;
   crack distal end position detection means for binary-coding the luminance levels of the video signal output from said scanning means in a direction perpendicular to the direction of the crack and thereafter discriminating a continuously obtained high-level value of said output to detect the crack distal end position; and
   crack distal end position calculating means for calculating a distance between the reference line position obtained by said reference line detection means and the crack distal end position obtained by said crack distal end position detection means.

3. A fatigue crack position detection method for use on a test piece on which a reference line is scribed, which comprises:
   calculating average luminance levels in the same direction as that of the reference line from a video signal,
   obtaining the video signal by scanning the fatigue test piece with the reference line during a fatigue test,
   binary-codeing the average luminance levels to obtain binary-coded data using a threshold value corresponding to a predetermined position in a normal direction of the reference line, and
   masking the average luminance levels by the binary-coded data to detect the position of the reference line.

4. A fatigue crack position detection apparatus, which comprises:
   scanning means for scanning a reference line and a crack in a fatigue test piece included within a field of view of the scanning means;
   a strobe illumination device for irradiating the fatigue test piece with illumination light;
   illumination control means for controlling an emission timing of said strobe illumination device to a predetermined timing;
   reference line detection means for integrating luminance levels from a video signal output obtained by a scanning operation of said scanning means in the same direction as that of the reference line to obtain a maximum level in the luminance levels, and to detect a reference line position;
   crack distal end postion detection means for binary-coding the luminance levels of the video signal output from said scanning means in a direction perpendicular to the direction of the crack and thereafter discriminating a continuously obtained high-level value of said output to detect a crack distal end position; and
   crack distal end postion calculating means for calculating a distance between the reference line position obtained by said reference line detection means and said crack distal end postion obtained by said crack distal end position detection means.

5. A fatigue crack position detection apparatus according to claim 4, wherein said strobe illumination device is arranged to be inclined at a predetermined angle with respect to a surface of the fatigue test piece so as to generate irregular reflected light by the crack and the reference line.

6. A fatigue crack position detection apparatus according to claim 4, wherein said illumination control means causes said strobe illumnation device to emit light at a time interval longer than an after-image time of said scanning means.

* * * * *